(12) United States Patent
Gilbert et al.

(10) Patent No.: US 8,145,439 B2
(45) Date of Patent: Mar. 27, 2012

(54) SUBSTANCE RELEASE ESTIMATION USING PATH-AVERAGED CONCENTRATION MEASUREMENTS

(75) Inventors: Ernest Gilbert, Simi Valley, CA (US); Shahryar Khajehnajafi, Moorpark, CA (US)

(73) Assignee: Safer Systems, L.L.C., Camarillo, CA (US)

( * ) Notice: Subject to any disclaimer, the term of this patent is extended or adjusted under 35 U.S.C. 154(b) by 601 days.

(21) Appl. No.: 12/187,235

(22) Filed: Aug. 6, 2008

(65) Prior Publication Data

US 2009/0055103 A1 Feb. 26, 2009

Related U.S. Application Data

(60) Provisional application No. 60/954,289, filed on Aug. 6, 2007.

(51) Int. Cl.
*G01N 31/00* (2006.01)
*G01J 5/02* (2006.01)
(52) U.S. Cl. .................................. 702/24; 250/341.8
(58) Field of Classification Search ............ 702/24, 702/22–23, 27–28, 30, 40, 49, 79, 81, 84, 702/127–128, 134, 137, 159, 170, 172, 179–183, 702/188–189, 199; 703/5, 12; 250/341.1, 250/341.8, 342, 390.04, 390.06, 393, 492.1
See application file for complete search history.

(56) References Cited

U.S. PATENT DOCUMENTS

| | | | |
|---|---|---|---|
| 4,924,095 A | 5/1990 | Swanson, Jr. | |
| 5,057,227 A | 10/1991 | Cohen | |
| 5,693,872 A | 12/1997 | Quinn | |
| 5,807,113 A | 9/1998 | Groeber | |
| 6,057,923 A | 5/2000 | Sachse | |
| 6,295,859 B1 | 10/2001 | Hayden et al. | |
| 6,455,851 B1 | 9/2002 | Lord et al. | |
| 6,772,071 B2 | 8/2004 | Gilbert et al. | |
| 7,566,881 B2 * | 7/2009 | Parvin et al. ................. | 250/394 |

FOREIGN PATENT DOCUMENTS

| JP | 2001-42052 | 2/2001 |
|---|---|---|
| WO | WO 00/33066 | 6/2000 |

OTHER PUBLICATIONS

Hashmonay et al., Field Evaluation of a Method for Estimating Gaseous Fluxes from Area Sources Using Open-Path Fourier Transform Infrared, 2001, Environmental Science & Technology, vol. 35, No. 11, pp. 2309-2313.*

(Continued)

*Primary Examiner* — Michael Nghiem
*Assistant Examiner* — Toan M Le
(74) *Attorney, Agent, or Firm* — Christie, Parker & Hale, LLP

(57) ABSTRACT

A system and method for using path-averaged concentration measurements for estimating the amount of substance being released from a particular location. One or more open-path sensing systems are set up in appropriate locations around possible substance release sites and tuned to detect a particular substance of interest. Path-averaged concentration measurements of the particular substance are collected over time and communicated to an open-path back calculation algorithm. The algorithm calculates time-averaged measurements for a plurality of time periods. Back calculation is then performed with the time-averaged measurements to estimate the release rate and the total release of the substance.

24 Claims, 10 Drawing Sheets

OTHER PUBLICATIONS

Nielsen et al., Concentration Fluctuations in Gas Releases by Industrial Accidents, May 2002, Riso National Laboratory, Roskilde, Denmark, 142 pp.*

Tohjima et al., Estimation of Methane Discharge From a Plume: A Case of Landfill, Geophysical Research Letters, Oct. 8, 1993, pp. 2067-2070, vol. 20, No. 19, Tokyo.

Lu et al., A Gis for Hazardous Chemicals Pathway Analysis, URISA Proceedings, 1995, pp. 293-299.

Winkler et al., Surveillance System for Air Pollutants by Combination Decision Support System COMPAS FTIR Optical Remote Sensing System K 300, 1997, pp. 369-380, Madrid.

Release Notice for 'Real Time 8.4', May 18, 2000.

Hashmonay, Optical Remote Sensing Technologies in the United States, EM, Nov. 2003, pp. 22-24.

Kahn et al., Next Century Challenges: Mobile Networking for "Smart Dust", Department of Electrical Engineering and Computer Sciences, University of California, Berkeley, 8 pages, 1999.

Safer Systems, Real-Time Integrated Software for Chemical Emergency Management, Protecting People . . . Protecting the Environment, Oct. 1997, 30 pages.

http://web.archive.org/web/20001005051332/safersystem.com/products.htmrl, XP-002396979, Safer Systems, LLC, Products, 1 page, Mar. 9, 1999.

Shell Global Solutions, http://www.shell.com/home/Framework?siteId=globalsolutions-en&FC2=FC3=/globalsol..., Light Touch, 2 pages, Downloaded on Jun. 8, 2007.

Segall et al., Radial Plume Mapping: An EPA method for area source emissions monitoring, 11 pages, 2005.

Takatsu, Patent Abstract of Japan, Publication No. 2001-042052, Published Feb. 16, 2001, U.S. Appl. No. 11/217,964, filed Jul. 30, 1999.

* cited by examiner

Puff crossing laser beam at different times

SUBSTANCE RELEASE ESTIMATION USING PATH-AVERAGED CONCENTRATION MEASUREMENTS

CROSS-REFERENCE

This application claims the benefit of U.S. Provisional Application No. 60/954,289, filed on Aug. 6, 2007, the content of which is incorporated herein by reference. This application also contains subject matter that is related to the subject matter in U.S. Pat. No. 6,772,071, the content of which is incorporated herein by reference.

FIELD OF THE INVENTION

This invention relates generally to computer-based estimation systems and, more specifically, to a system and method for estimating the release rate of a substance using path-averaged concentration measurements.

BACKGROUND OF THE INVENTION

U.S. Pat. No. 6,772,071 discloses a system and method for estimating the amount of substance released into a surrounding medium from a known location. The system includes a network of point sensors that are configured to take concentration measurements over time. These measurements are then used with a dispersion model to estimate the release rate (and total release) of the substance via a back calculation algorithm. This technique is particularly suitable for gaseous substances, especially toxic chemicals, where the release rate information can dictate the scope and speed of any necessary response.

Toxic substances often travel far and large. Covering such areas and distances via point sensors alone may require a large number of such sensors to be placed along the area or distance. As the number of required sensors increase, so does the cost of monitoring the large areas. Accordingly, what is desired is a system and method for substance release estimation for covering large areas in a more efficient manner than what is currently provided via point sensors alone.

Furthermore, the rate in which substances are released into the environment are affected by atmospheric conditions such as wind speed, solar radiation, and the like. Accordingly, it is desirable to have a system and method for substance release estimation that takes into account such atmospheric changes.

SUMMARY OF THE INVENTION

The present invention is directed to a computer-implemented substance release estimation method for a substance released into a surrounding medium thereby creating a plume. The method includes calculating a plurality of path-averaged concentration measurements of the substance for a plurality of time instants; averaging the plurality of path-averaged concentration measurements over the plurality of time instants to obtain a time-averaged measurement of the plurality of path-averaged concentration measurements; and estimating a release rate of the substance as a function of the time-averaged measurement of the plurality of path-averaged concentration measurements.

According to one embodiment of the invention, the method further includes assuming a release rate of the substance; modeling the plume based on the assumed release rate; and predicting a width of the plume at each of the plurality of time instants based on the modeling of the plume.

According to one embodiment of the invention, the modeling of the plume adjusts to changes to atmospheric conditions including wind direction, wind speed, and stability over time.

According to one embodiment of the invention, the calculating of the plurality of path-averaged concentration measurements includes collecting a plurality of concentrations of the substance measured at each of the plurality of time instants; and dividing each of the collected plurality of concentrations by the predicted width of the plume at the corresponding one of the plurality of time instants.

According to one embodiment of the invention, the collecting the plurality of concentrations includes transmitting a beam of light; and determining an amount of the light absorbed by the substance along the path of the beam.

According to one embodiment of the invention, the estimating of the release rate further includes predicting one or more path-averaged concentrations of the substance at each of the plurality of time instants based on the modeling of the plume; averaging the predicted path-averaged concentrations over the plurality of time instants to generate a time-averaged prediction of the predicted path-averaged concentrations; comparing the time-averaged prediction of the predicted path-averaged concentrations with the time-averaged measurement of the plurality of path-averaged concentration measurements; and selecting the assumed release rate as the estimated release rate of the substance based on the comparing.

According to one embodiment, the substance may be a single gas or a chemical mixture including a plurality of gases. In a multi-component mixture, concentration measurements of each of the plurality of gases are received from at least one open-path sensor; and chemical properties of the chemical mixture are dynamically identified based on the received concentration measurements. The release rate that is estimated is then for the entire chemical mixture.

According to another embodiment, the present invention is directed to a substance release estimation system for a substance released into a surrounding medium thereby creating a plume. The system includes at least one sensing system configured to collect a plurality of concentrations of the substance measured at each of a plurality of time instants, and a computer operably coupled to the at least one sensing system. The computer is configured to execute computer program instructions stored in memory that calculate a plurality of path-averaged concentration measurements based on the collected plurality of concentrations; average the plurality of path-averaged concentration measurements over the plurality of time instants to obtain a time-averaged measurement of the plurality of path-averaged concentration measurements; and estimate a release rate of the substance as a function of the time-averaged measurement of the plurality of path-averaged concentration measurements.

According to one embodiment of the invention, the sensing system may include an open-path sensor, or include both fixed point and open-path sensors.

A person of skill in the art should recognize that the system and method for substance release estimation according to the various embodiments of the present invention allows accurate prediction of the release rate of a single chemical or a multi-component chemical mixture, where the chemical or chemical mixture is released into a dynamic environment where there might be changes in the atmospheric condition (e.g. changes in wind direction, speed, etc.) over time. By incorporating a time factor into the estimation analysis, the predicted release rate takes those atmospheric changes into account, for a more accurate prediction of the release rate.

DETAILED DESCRIPTION

Figure 1:
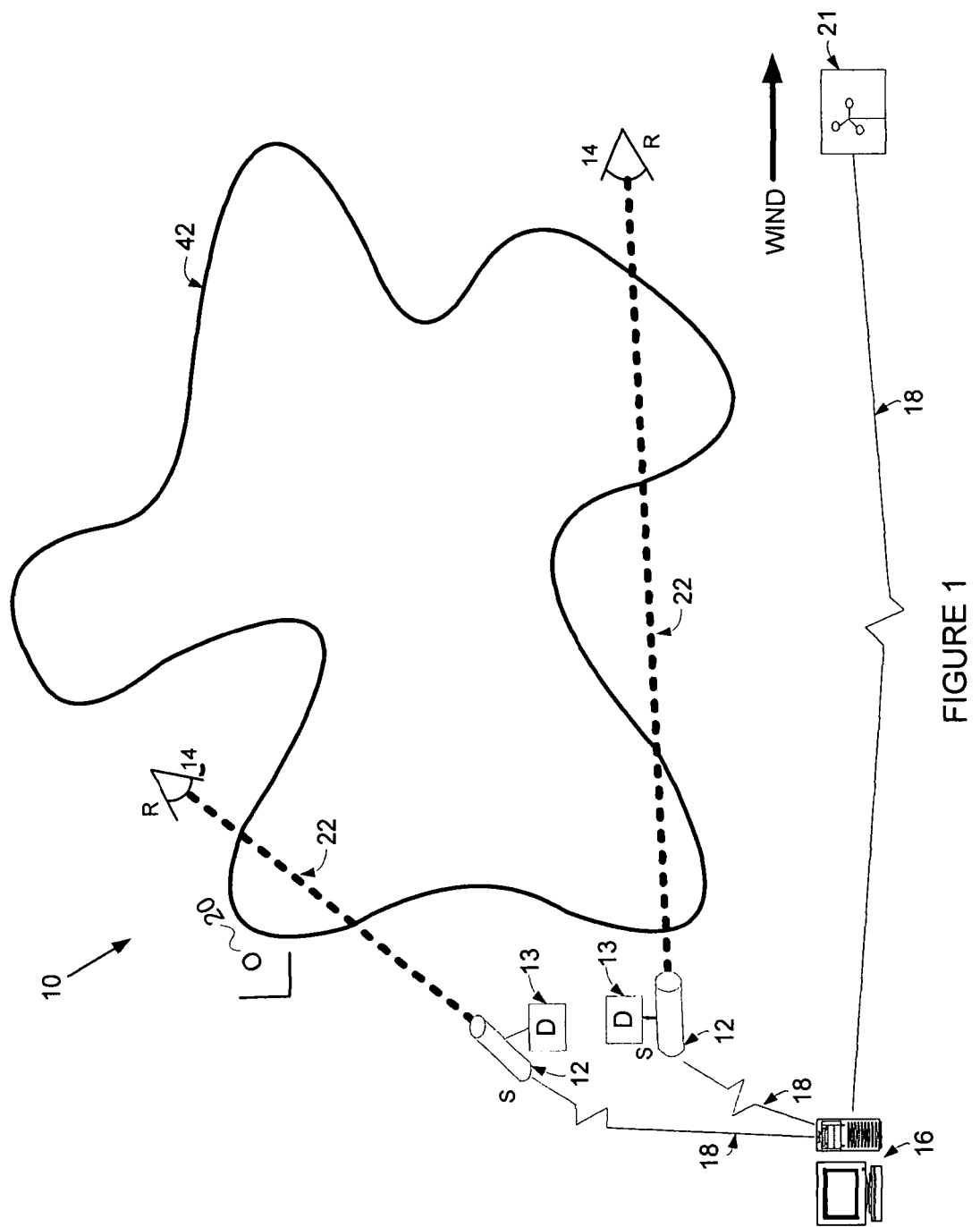
FIG. 1 is a diagram of an open-path substance release estimation system according to one embodiment of the invention.

An embodiment of the present invention applies path-averaged concentration measurements for estimating the rate in which a substance is released from a particular source. The release rate estimate according to embodiments of the present invention is time-dependent in order to account for any changes of loss of containment conditions over time. The predicted release rate is then provided to a dispersion model in order to calculate the overall plume impact.

The substance for which a release rate is estimated may be, for example, a toxic chemical in a gaseous or liquid state. In addition, the substance may be a pure gas or a multi-component mixture containing multiples gases. According to one embodiment, one or more open-path sensing systems are set up in appropriate locations around possible substance release sites and tuned to detect a particular substance of interest. An open-path sensing system includes any system that includes a remote sensor that detects and/or measures the concentration of a substance in the air that crosses a beam of light by the amount of the light absorbed by the substance.

Open-path sensing systems are desirable for monitoring large areas and/or long distances as opposed to other types of sensors because of their ability to sense concentrations along a path. Thus, a single system may be used to monitor levels of concentrations along a long path instead of requiring, for example, multiple point sensors to be placed over the same path. Furthermore, open path sensing systems may monitor concentrations in any type of terrain including complex terrains Open-path sensing systems are also desirable because they experience almost no monitoring lag, are capable of detecting a wide spectrum of gases, and experience little gas interference issues. A person of skill in the art should recognize that although open-path sensors are preferred, embodiments of the present invention may also include point sensors working in combination with open-path sensors.

During either routine monitoring or in response to a substance release, total concentration measurements of a particular substance are collected by the open-path sensing systems at various time instants and communicated to a computer programmed with an open-path back calculation algorithm in a relatively quick and accurate manner. The algorithm calculates path-averaged concentrations of the plume for the various time instants and smoothes out the path-averaged concentrations from the collection of substantially instantaneous measurements to a more consistent set of time-averaged measurements. Back calculation is then performed with the time-average of the path-averaged ("TAPA") measurements to estimate the release rate and the total release of the substance for each open-path sensing system. According to one embodiment, the back calculation starts off with an assumed rate of release of the substance and predicts a TAPA concentration of the substance for one or more time windows based on a selected dispersion model. The assumed rate is recursively modified until the predicted measurements sufficiently converge with the TAPA measurements for a particular open-path sensing system. When the measurements sufficiently converge, the assumed rate is set as the actual release rate.

FIG. 1 is a diagram of an open-path substance release estimation system 10 for estimating a release rate of a substance released from a location 20 thereby generating a plume 42. The open-path substance release estimation system 10 includes one or more open-path sensing systems that detects and/or measures the concentration of a substance in the air through which light passes. One or more of the open-path sensing systems may be fixed systems which are designated to continuously monitor within or near the source of emission. One or more of the open-path sensing systems may also be portable systems which may be proactively positioned downstream of the source of an emission once the emission occurs. Portable sensors allow the system to be easily scalable based on the magnitude of the release. In addition, one or more of the open-path sensing systems may be equipped with motorized guidance hardware and software for measuring concentrations along a path of a first area, and automatically reconfiguring the location of the open-path sensing system for measuring concentrations along a path of a second area. This allows a single open-path sensing system to automatically monitor a large area in an efficient manner. One or more of the open-path sensing systems may also be located at any elevation for measuring concentrations at any height off of the ground. For example, the sensing system(s) may be placed on ground level for measuring ground level emissions, or at elevated levels for measuring emissions above the ground.

According to one embodiment of the invention, each open-path system includes a radiation source 12, detection unit 13, and reflector 14. The radiation source 12 may be a tunable diode laser, infrared device, or any light source capable of emitting infrared, visible, and/or ultraviolet light. The reflector 14 may be any device conventional in the art configured to reflect light, such as, for example, one or more cubic gold plated mirrors. According to one embodiment, each reflector 14 is positioned so that the incoming light from the radiation source 12 is parallel to the reflected light. A maximum distance between the radiation source 12 and the reflector 14 may be, for example, 1000 meters. Thus, a single open-path sensing system is capable of monitoring concentrations along a path that may be up to 1000 meters long.

The light reflected by the reflector 14 is received by the detection unit 13. The detection unit 13 is configured to detect the intensity of the reflected light. According to one embodiment of the invention, the radiation source 12 and detection unit 13 are included within a single housing. According to another embodiment of the invention, the radiation source 12 and detection unit 13 are included in separate housings. The detection unit 13 detects and processes the intensity of the reflected light to calculate the concentration of the substance passing through the light. According to another embodiment of the invention the processing of the intensity information is performed by a separate processing unit, such as, for example, computer 16.

According to one embodiment of the invention, each open-path sensing system is coupled to the computer 16 over a data communications network 18. The data communications network 18 may be a local area network (LAN), private wide area network (WAN), the Internet, or any wired or wireless network environment conventional in the art. According to one embodiment of the invention, the computer 16 includes a memory that stores computer program instructions which, when executed by a processor, cause the computer to control the operation of the open-path sensing system. According to one embodiment of the invention, the computer invokes the open-path sensing system to collect concentration measurements of a particular substance in the air through which light passes at multiple time instants, and further averages or causes averaging of the concentration measurements based on the varying cross-sections of the plume crossing the light path at the various time instants to generate path-averaged concentration measurements. The computer 16 is also configured with program instructions that implement the open-path back calculation algorithm to estimate the release rate of the particular substance based on the obtained path-averaged concentration measurements.

The computer 16 may further be coupled to optional weather sensors 21 that provide meteorological data such as wind speed and direction to the computer over the wired or wireless data communications network. Such information may alternatively be obtained from other sources such as, for example, the Internet. According to one embodiment of the invention, the wind speed and direction information are provided to the open-path back calculation algorithm for calculation of the release rate.

In general terms, the open-path sensing system works based on a spectroscopic principle. That is, most gases have unique spectroscopic absorption features that are detectable by the sensing system. In the embodiment where the radiation source 12 is a tunable laser, the laser is tuned to emit a laser beam 22 of a particular wavelength that is known to be absorbed by the substance to be measured. The beam is reflected by the reflector 14 and received by the detection unit 13. The detection unit detects the intensity of the reflected beam which indicates the amount of light absorbed by the substance, and processes this information to calculate the measure of the concentration of the substance. The detection unit 13 further measures the total amount of a specific gas over the distance traveled by the laser beam, and outputs this information as ppm-m. The path-averaging calculation is then performed by a separate processing unit, such as, for example, the computer 16.

Laser devices are particularly suitable as the radiation source 12 for path-averaged sensing because they can be precisely tuned to measure the concentrations of particular substances. However, because lasers provide instantaneous values of the concentration, the values are not steady for transient plumes and fluctuate significantly from one measurement to the next depending on the dynamics of the plume. According to one embodiment of the invention, time-averaging is employed to overcome these fluctuations and produce more consistent measurements.

Figure 2:
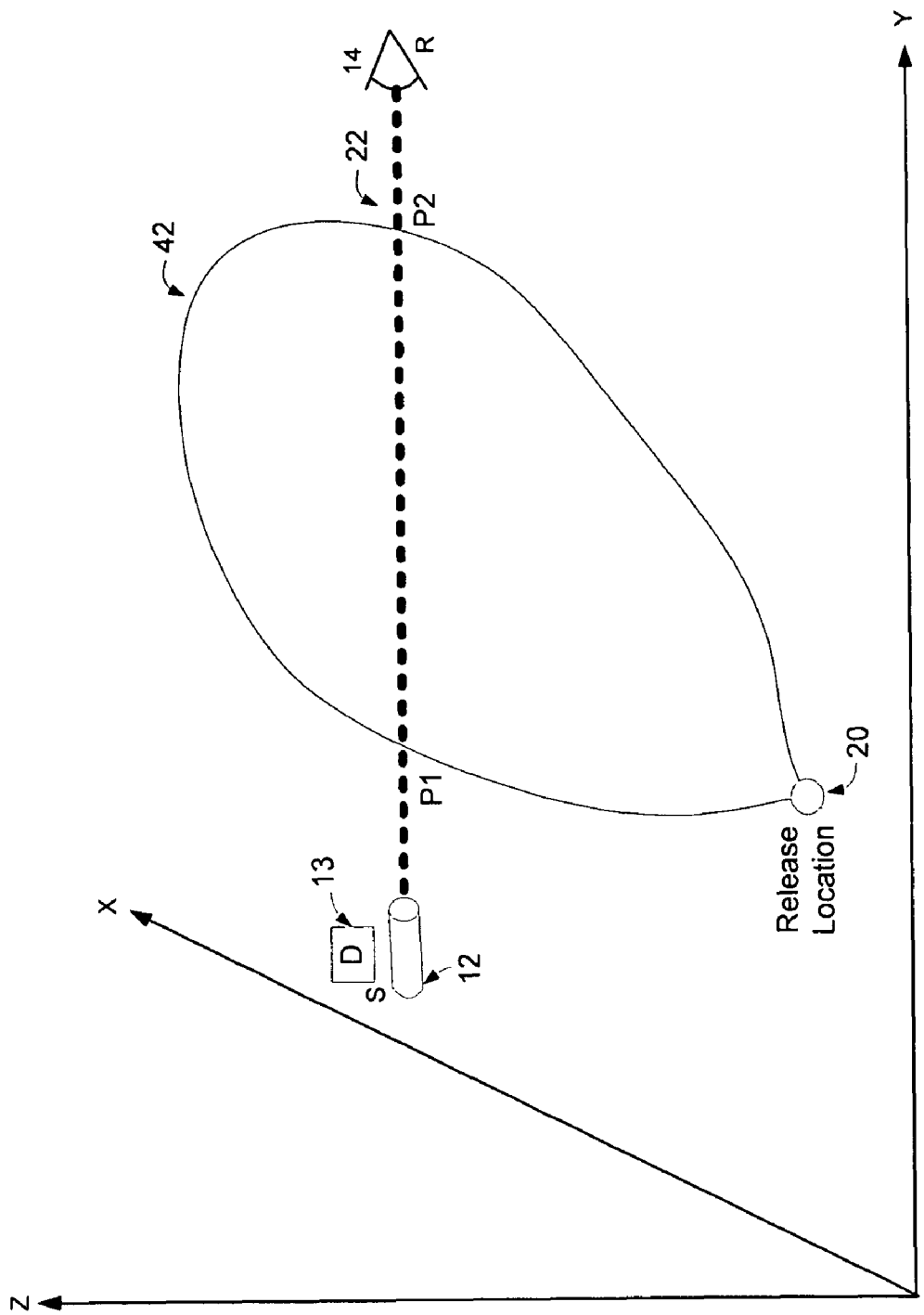
FIG. 2 illustrates an exemplary steady state plume crossing a beam projected by an open-path sensing system.

FIG. 2A illustrates an exemplary steady state chemical plume 42 crossing a beam 22 projected by one of the radiation sources 12. The detection unit 13 measures the concentration of the substance in the path between the radiation source 12 and the reflector 14. In this regard, the radiation source 12 is tuned to the absorption wavelength of the particular substance released from the release location 20. The source 12 emits the beam of light at the tuned frequency, and the detection unit 13 measures the amount of light absorbed by the plume 42 along the path of the beam 22. According to one embodiment of the invention, the amount of light absorbed is a measure of the concentration of the substance along the path of the beam. A path-averaged concentration is then obtained by the computer 16 dividing the measure of the concentration by the plume width.

According to one embodiment of the invention, the path-averaged concentration of the plume that is generated from the total path concentration measurement provided by the open-path sensing system (referred to as the measured path-averaged concentration) is defined by the following formula:

$$\overline{C}_L = \frac{C_m}{X} \tag{1}$$

where $C_m$ is a total path concentration measurement along the path of the beam 22 from the source 12 and reflector 14 positions, and X is the predicted plume width.

The path-averaged plume concentration that is to be predicted based on a dispersion model selected by the open-path back calculation algorithm (referred to as the predicted path-averaged concentration) may be defined by the following formula:

$$C_p = \frac{\int_{P1}^{P2} C_p(x)dx}{X} \tag{2}$$

where P1 and P2 represent the location where the plume 42 intersects the beam 22, and C is a predicted concentration. Accurate predictions of the concentration are possible when the plume intersects the beam at two points.

The situation illustrated in FIG. 2A is an ideal situation where the plume is in a steady state. However, in most industrial cases, the plume is transient, making the plume concentration a function of both time and position.

Figure 3:
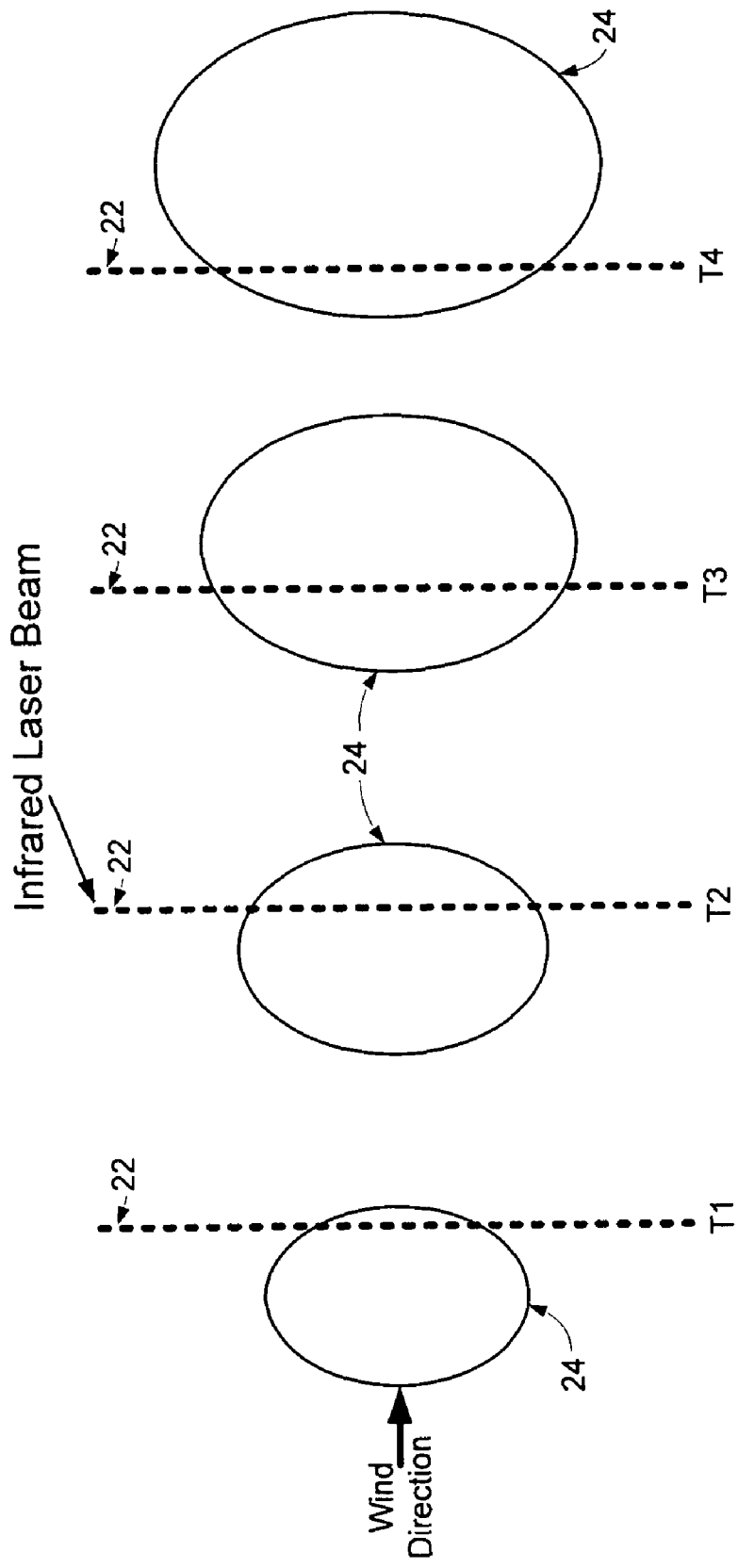
FIG. 3 illustrates puffs of a transient plume crossing a beam projected by an open-path sensing system at different times.

FIG. 3 illustrates puffs 24 of a transient plume 42 crossing the beam 22 generated by the open-path sensing system at different time instants. This figure illustrates puffs crossing the beam that is generated by one open-path sensing system. As mentioned, the plume measurements may be taken from multiple open-path sensing systems. Due to the movement of the plume based on wind velocity and other atmospheric factors, the cross section formed due to the puff intersecting the beam varies from one time instant to another, causing the measured and predicted concentrations along the path of the beam 22 to also adjust accordingly to accurately predict the release rate over time.

The measured path-averaged concentration that takes into account the time and position of the plume 42 may be defined by the following formula:

$$\overline{C}_L(t) = \frac{C_m(t)}{X} \tag{3}$$

The predicted path-averaged concentration that takes into account the time and position of the plume 42 may be defined by the following formula:

$$C_p(t) = \frac{\int_{P1}^{P2} C_p(x, t)dx}{X} \quad (4)$$

Due to the nature of open-path sensors, the concentration measurement at a particular point in time is substantially instantaneous. Thus, the measurements may greatly fluctuate from one point in time to another. According to one embodiment of the invention, the measured path-averaged concentration measurements collected for multiple time instants within a particular time window are averaged over the time window to reduce the fluctuations and generate the TAPA concentration for the time window (referred to as the measured TAPA concentration). Similarly, the predicted path-averaged concentration measurements for the same time instants are averaged over the time window to generate the predicted TAPA concentration for the time window.

The measured TAPA concentration may be defined by the following formula where T is the total time interval:

$$C_L = \frac{\int_{t1}^{t2} \overline{C_L(t)} dt}{T} \quad (5)$$

The predicted TAPA concentration may be defined by the following formula:

$$C_P = \frac{\int_{t1}^{t2} \overline{C_P(t)} dt}{T} \quad (6)$$

By choosing a suitable time interval over which to average, such as, for example, 60 seconds, numerous path-averaged measurements may be collected and reduced to a set of TAPA measurements for each sensor that better fit an ideal dispersion pattern and allow back calculation to be performed. A person of skill in the art should appreciate that the amount of data collected and processed may vary depending on current processing technologies and efficiency requirements.

Figure 4A:
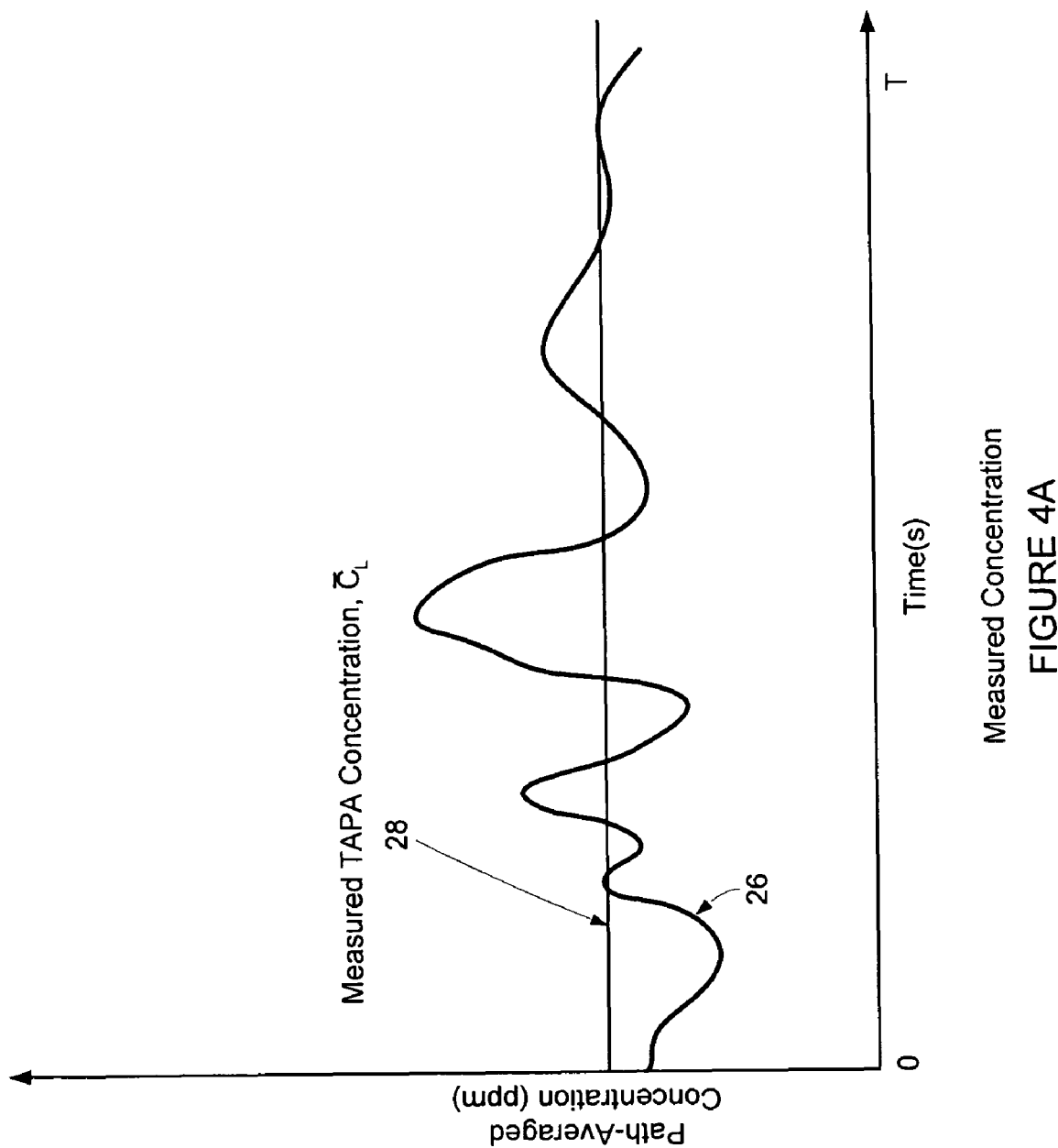
FIG. 4A is a graph with exemplary measurements of path-averaged concentrations and a corresponding averaged value over time.

FIG. 4A is a graph with exemplary path-averaged concentration measurements taken by the open-path sensing system over time. As is illustrated by line 26, the measured path-averaged concentrations may change from one time instant to another due to the movement of the plume 42. However, a fairly good average develops over time, as is illustrated by line 28 depicting a measured TAPA concentration value.

Figure 4B:
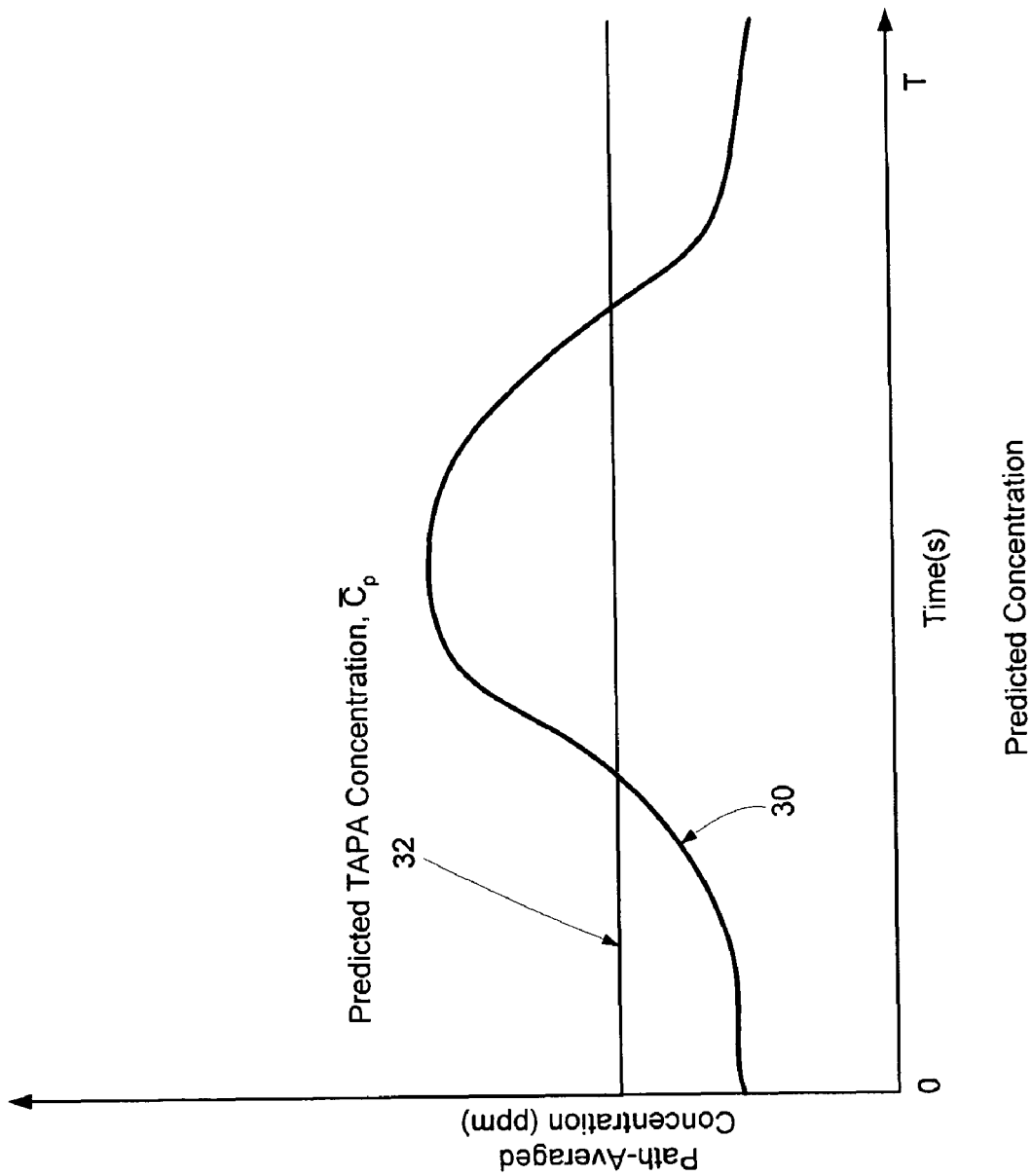
FIG. 4B is a graph with exemplary predicted path-averaged concentrations and a corresponding averaged value over time.

FIG. 4B is a graph with exemplary predicted path-averaged concentrations over time. As is illustrated by line 30, the path-averaged concentrations predicted by the selected dispersion model is much smoother than the actual path-averaged measurements. In order to compare the predicted concentrations against the measured concentrations, however, the predicted path-averaged concentrations are also time-averaged to obtain the predicted TAPA concentration as is reflected by line 32.

Depending on the placement of a particular open-path sensor and the trajectory and width of the plume, concentration measurements via a single open-path sensor may not be sufficient to cover the entire plume. In order to ensure that no boundary of the cloud (P1, P2) can traverse without measurement, embodiments of the present invention support multiple open path measurements via multiple open-path sensors.

Figure 5:
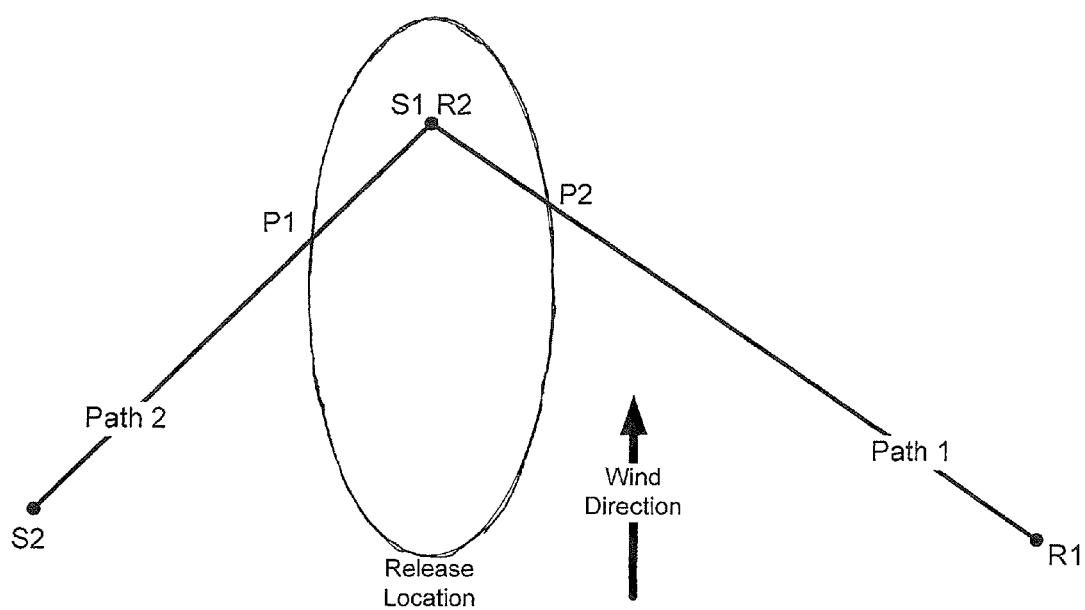
FIG. 5 illustrates an exemplary plume being monitored by multiple open-path sensing systems according to one embodiment of the invention.

FIG. 5 depicts a situation where the concentration measurement along path 1 only accounts for a first portion of the cloud while the concentration measurement along path 2 only accounts for a second portion of the cloud. The combination of the open path measurements along path 1 and path 2 therefore ensure that the entire cloud is monitored as the cloud crosses paths 1 and 2. According to one embodiment of the invention, the concentration measurements along the two paths are combined in calculating the TAPA concentration.

Figure 6:
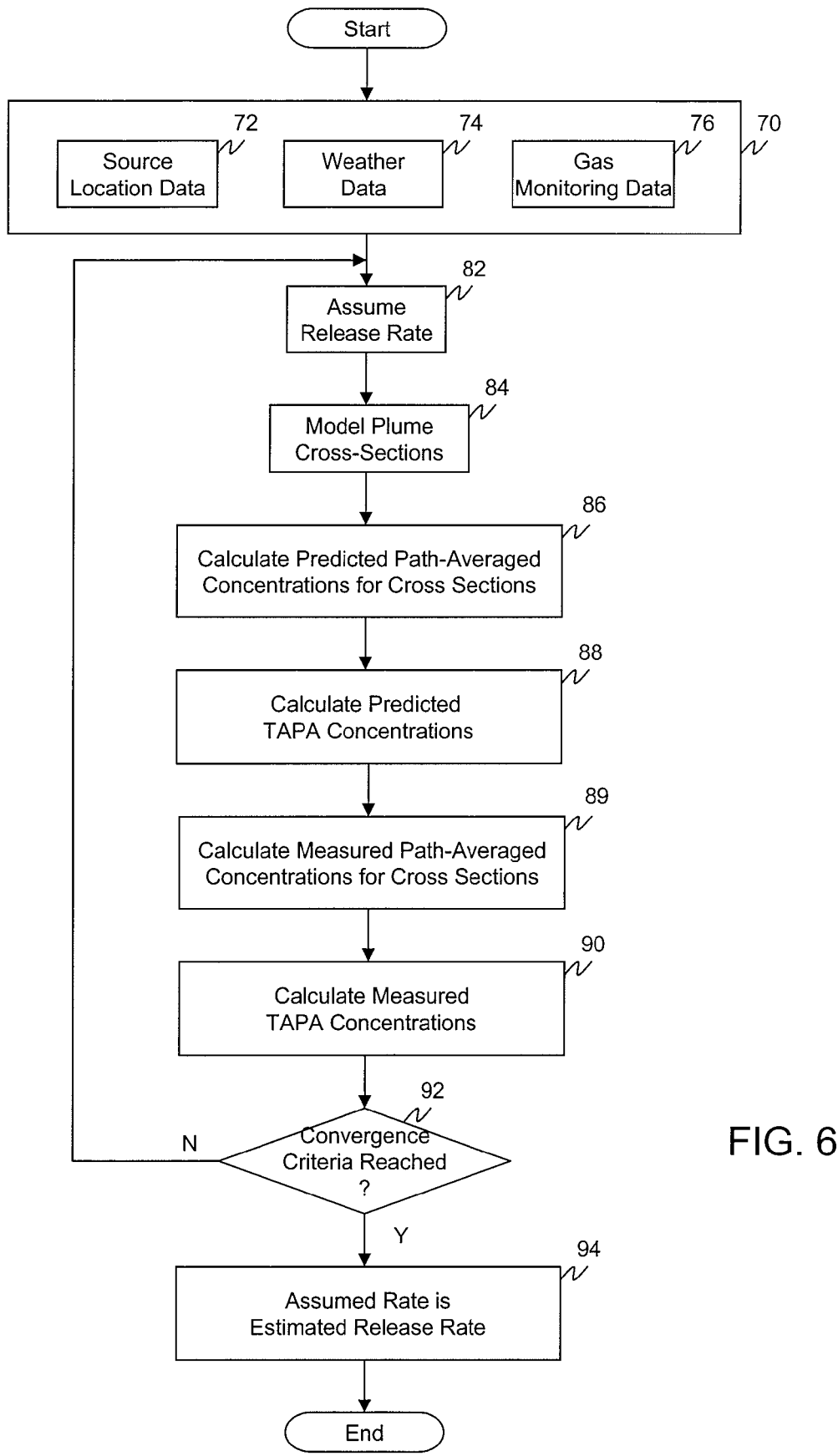
FIG. 6 is a process flow diagram of an open-path release rate estimation algorithm according to one embodiment of the invention.

FIG. 6 is a process flow diagram of an open-path back calculation algorithm implemented by the computer 16 for predicting the release rate according to one embodiment of the invention. The steps of the process may be implemented in the order indicated, or in any other order recognized by a person of skill in the art.

In step 70, various types of input data are gathered by the computer, including, for example, source location data 72, weather data 74, and gas monitoring data 76. According to one embodiment of the invention, the source location data 72 includes the substance release location and information on the chemical that is being released. The weather data 74 includes wind speed, wind direction, stability (e.g. measure of atmospheric turbulence), and other atmospheric information. The gas monitoring data 76 includes total path concentration data from each open-path sensing system such as, for example, the various times of the measurement, amount of measured concentration at each time, and locations of the radiation source 12 and reflector 14. Processing then proceeds to the back calculation process in steps 82-94 for each of the open-path sensing systems. In step 82, the process assumes a release rate of the identified chemical. The initial release rate may be a randomly selected, a predetermined default rate, or the like.

In step 84, the plume 42 that is generated by the substance release is modeled based on a selected dispersion model. The dispersion model takes into account the source location data 72, weather data 74, and/or gas monitoring data 76 to generate the plume model. According to one embodiment of the invention, the dispersion model is a Lagrangian integrated puff model. According to this model, puffs of the plume are released a minute apart and their trajectories followed as they are moved by the wind velocity. Various factors such as wind direction, stability, and the like, may be considered in generating the plume model. The cross-section of a puff crossing the beam at different time instants is then modeled. The plume model therefore provides the predicted intersection points of the plume with the beam, and from this information, the plume width is predicted for the different time instants.

In step 86, the process calculates the predicted path-averaged concentrations of the plume cross-sections at different time instants within a particular time window, such as, for example, 60 seconds. According to one embodiment of the invention, the calculation is based on formula (2) discussed above.

In step 88, the predicted TAPA concentration is calculated for the time window for the various predicted path-average concentrations. According to one embodiment of the invention, the calculation is based on formulas (4) and (6) discussed above.

In step 89, the process calculates the path-averaged concentrations from the total path measurements collected at the different time instants by the corresponding sensing system.

According to one embodiment of the invention, the calculation is based on formula (1) discussed above.

In step 90, the measured path-averaged concentrations are time-averaged to produce measured TAPA concentration for the same time window. According to one embodiment of the invention, the calculation is based on formulas (3) and (5) discussed above. According to another embodiment of the invention, the path-averaging and/or the TAPA calculations are performed directly by the detector unit 13 and provided to the computer 16 as part of the instrumentation input 76.

In step 92, each of the plurality of predicted and measured TAPA concentrations are compared for determining whether a convergence criteria has been reached. According to one embodiment, the formula for determining whether the convergence criteria has been reached is as follows:

$$\Delta C = \left| \frac{\overline{C}_L - \overline{C}_P}{\overline{C}_L} \right| \leq \varepsilon \tag{7}$$

where $\overline{C}_L$ and $\overline{C}_P$ are respectively the measured and predicted TAPA concentrations, and $\varepsilon$ is the convergence criteria. According to one embodiment of the invention, a weight may also be assigned for each sensor as a function of its position.

The open-path back calculation algorithm seeks to minimize the difference between the measured and predicted concentrations. In other words the actual release rate is obtained by minimizing the error:

$$\frac{\partial (\Delta C)}{\partial Q} = 0 \tag{8}$$

If the predicted and measured TAPA values for a sufficient number of time windows satisfy the convergence criteria, the rate assumed in step 82 is deemed to be a good estimate of the actual release rate, and in step 94, the assumed rate is set to be the actual release rate for the particular sensing system. Otherwise, the process returns to step 82 where a new release rate is assumed. In this regard, the prior assumed rate may be increased or decreased by fixed amounts, variable amounts, or a combination of the two. The process is executed for each of the various open-path sensing systems for obtaining the estimated release rate (and the estimated total release) for each open-path sensing system. Once the estimated release rate is obtained for each open-path sensing system, the estimated release rate and its associated time may be plugged into the dispersion model as described in the above-referenced U.S. Pat. No. 6,772,071 for overall plume effect.

According to one embodiment of the invention, the above-described system and method for predicting the release rate of a substance applies to a pure gas, or a multiple gas composition. Substance release estimation via back calculation for multi-gas measurements poses a couple of unique challenges. These challenges include dynamically creating a chemical mixture from the measured compositions, and dynamically defining isopleths limits for the gas mixture. In performing release rate estimation via point sensors and an open-path single component, the gas being monitored is known and its isopleths are defined a priori. However, for an open-path multi-gas monitoring system, the chemicals are dynamically identified when a gas stream passes through the beam projected by an open-path sensor.

According to one embodiment of the invention, when a gas mixture is passed through an open-path sensing system (e.g. FTIR or broad spectrum UV), the system dynamically identifies the chemical makeup of the gas stream along with the molar composition of each species (i.e. individual gas component) in the stream. This information is utilized to figure out the chemical composition of the gaseous stream at the source. The substance release estimation system then uses the derived pseudo-chemical properties for release rate estimation.

According to one embodiment of the invention, the identification of the chemical composition of the gas stream is based on a ten minute running average. That is, the system dynamically scales to the detected chemicals and their concentrations up to ten minutes. After ten minutes, the makeup of the composition is deemed to be fixed, and only the rate of the composition changes. A person of skill in the art should recognize that other time windows may be used instead of the ten minute time window.

The identification of the chemical composition of the gas stream includes the generating of a table with the concentration of each gas contained in the gas stream. The concentration is detected and provided by one or more of the open-path sensing systems. Table 1 is an example of such a table. According to one embodiment, the table includes a predetermined number of fields (e.g. 10) and rows. According to one embodiment, each field represents the concentration data averaged over one minute. Each row represents a chemical composition variation for a detected chemical over ten minute periods. The last row of the table contains the release rate estimated for each one minute period using the back calculation algorithm. In order to estimate the release rate via the back calculation algorithm, the chemical properties of the gas mixture must be provided. The method of dynamically deriving such chemical properties (referred to as pseudo-chemical properties) is described below with reference to an exemplary gas mixture composed of 10 species.

Assume we are 20 minutes into the event and the open-path substance release estimation system tries to estimate the release rate of the gas mixture. A "ten minute" table (Table 1) based on the previously gathered information is formed via the computer 16. According to one embodiment, the entries of Table 1 are volume based.

TABLE 1

Variation of one minute molar averaged concentration of species over ten minutes

| Time (sec) | 60 | 120 | 180 | 240 | 300 | 360 | 420 | 480 | 540 | 600 |
|---|---|---|---|---|---|---|---|---|---|---|
| Conc. Species 1 (ppm) | C11 | C12 | C13 | C14 | C15 | C16 | C17 | C18 | C19 | C110 |
| Conc. Species 2 (ppm) | C21 | C22 | C23 | C24 | C25 | C26 | C27 | C28 | C29 | C210 |
| Conc. Species 3 (ppm) | C31 | C32 | C33 | C34 | C35 | C36 | C37 | C38 | C39 | C310 |
| Conc. Species 4 (ppm) | C41 | C42 | C43 | C44 | C45 | C46 | C47 | C48 | C49 | C410 |

TABLE 1-continued

Variation of one minute molar averaged concentration of species over ten minutes

| Time (sec) | 60 | 120 | 180 | 240 | 300 | 360 | 420 | 480 | 540 | 600 |
|---|---|---|---|---|---|---|---|---|---|---|
| Conc. Species 5 (ppm) | C51 | C52 | C53 | C54 | C55 | C56 | C57 | C58 | C59 | C510 |
| Conc. Species 6 (ppm) | C61 | C62 | C63 | C64 | C65 | C66 | C67 | C68 | C69 | C610 |
| Conc. Species 7 (ppm) | C71 | C72 | C73 | C74 | C75 | C76 | C77 | C78 | C79 | C710 |
| Conc. Species 8 (ppm) | C81 | C82 | C83 | C84 | C85 | C86 | C87 | C88 | C89 | C810 |
| Conc. Species 9 (ppm) | C91 | C92 | C93 | C94 | C95 | C96 | C97 | C98 | C99 | C910 |
| Conc. Species 10 (ppm) | C101 | C102 | C103 | C104 | C105 | C106 | C107 | C108 | C109 | C1010 |
| Release Rate (kg/s) | R1 | R2 | R3 | R4 | R5 | R6 | R7 | R8 | R9 | R10 |

From Table 1, the computer 16 forms a second table (Table 2) with entries based on mass fraction.

TABLE 2

Variation of one minute mass averaged concentration of each species over ten minutes

| Time (sec) | 60 | 120 | 180 | 240 | 300 | 360 | 420 | 480 | 540 | 600 |
|---|---|---|---|---|---|---|---|---|---|---|
| Conc. Species 1 (% wt) | X11 | X12 | X13 | X14 | X15 | X16 | X17 | X18 | X19 | X110 |
| Conc. Species 2 (% wt) | X21 | X22 | X23 | X24 | X25 | X26 | X27 | X28 | X29 | X210 |
| Conc. Species 3 (% wt) | X31 | X32 | X33 | X34 | X35 | X36 | X37 | X38 | X39 | X310 |
| Conc. Species 4 (% wt) | X41 | X42 | X43 | X44 | X45 | X46 | X47 | X48 | X49 | X410 |
| Conc. Species 5 (% wt) | X51 | X52 | X53 | X54 | X55 | X56 | X57 | X58 | X59 | X510 |
| Conc. Species 6 (% wt) | X61 | X62 | X63 | X64 | X65 | X66 | X67 | X68 | X69 | X610 |
| Conc. Species 7 (% wt) | X71 | X72 | X73 | X74 | X75 | X76 | X77 | X78 | X79 | X710 |
| Conc. Species 8 (% wt) | X81 | X82 | X83 | X84 | X85 | X86 | X87 | X88 | X89 | X810 |
| Conc. Species 9 (% wt) | X91 | X92 | X93 | X94 | X95 | X96 | X97 | X98 | X99 | X910 |
| Conc. Species 10 (% wt) | X101 | X102 | X103 | X104 | X105 | X106 | X107 | X108 | X109 | X1010 |
| Release Rate (kg/s) | R1 | R2 | R3 | R4 | R5 | R6 | R7 | R8 | R9 | R10 |

Pseudo chemical properties are calculated based on 10 minute data. A table of weight fraction from the table of mole fraction is created as follows:

For example, for species 1 the weight fraction Y1 is calculated as follows:

$$S1 = R1*X11 + R2*X12 + R3*X13 + R4*X14 + R5*X15 + R6*X16 + R7*X17 + R8*X18 + R9*X19 + R10*X10$$

$$Y1 = S1/(S1 + S2 + S3 + S4 + S5 + S6 + S7 + S8 + S9 + S10)$$

where, S1 is the cumulative release of species 1 up to 10 minutes. R1 is the estimated release rate of the gas stream for time 1, R2 is the estimated release rate for the gas stream for time 2, and so forth, and X11 is the mass averaged concentration of species 1 for the first minutes, X12 is the mass averaged concentration of species 1 for the second minute, and so forth. This procedure is used to calculate the weight fraction of other species for a ten minute period. The weight fractions are then converted to mole fractions to get a final composition of the gas mixture. A mixing rule, which expresses a mixture parameter in terms of composition and pure component parameter is used to calculate the chemical properties of the pseudo-chemical. The created pseudo-chemical is then used in the calculation of the release rate at 20 minutes into the simulation.

Figure 7:
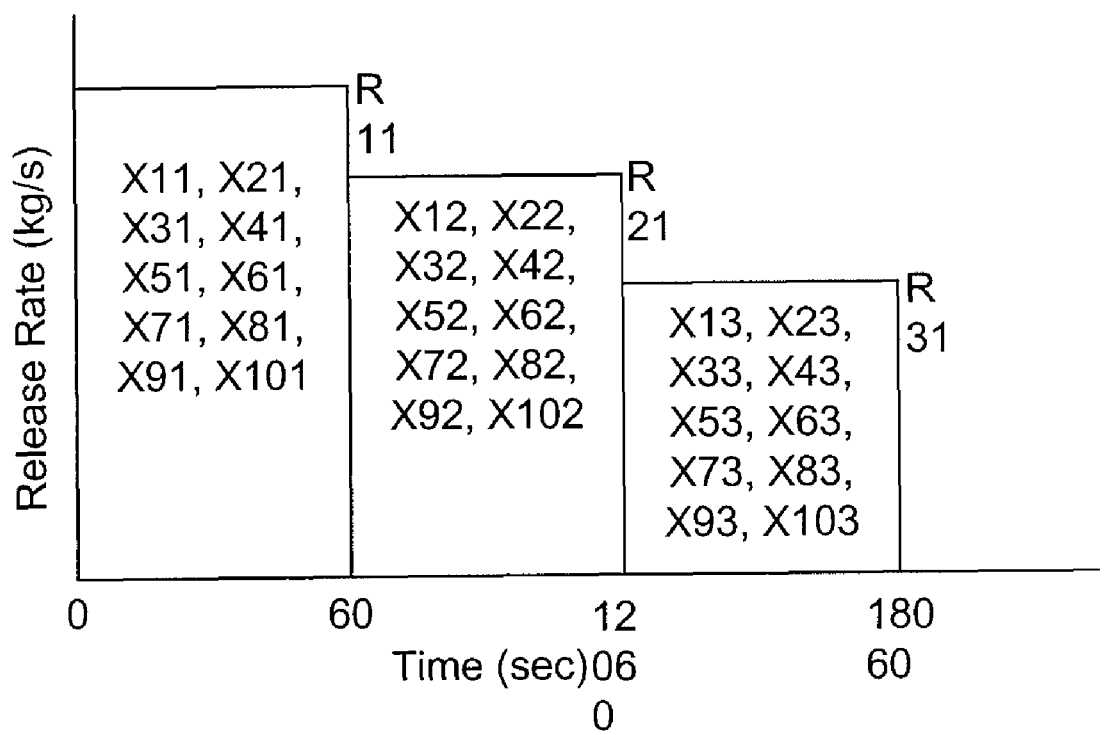
FIG. 7 is a graphical representation of mass fractions of various gas components, in this case ten components, in a multi-gas composition over a 3 minutes period according to one embodiment of the invention.

The release rate and composition of the release stream that is calculated may be graphically represented as is illustrated in FIG. 7.

According to one embodiment of the invention, for simulation times of less than 10 minutes, e.g. 180 seconds, the data from time zero up to a minute before current simulation time, in this case 120 seconds, are used to form the pseudo-chemical properties.

To run the dispersion model, after the release rate is estimated, the isopleths needed for dispersion are dynamically setup which reflect the composition of the gas stream. According to one embodiment of the invention, the following formula is used to calculate a Toxic Limit Value of the mixture:

$$TLV(\text{mixture}) = \frac{1}{\frac{f_a}{TLV_a} + \frac{f_b}{TLV_b} + \frac{f_c}{TLV_c} + \cdots \frac{f_n}{TLV_n}}$$

The TLV is calculated based on percent composition (by weight) of the gas mixture, where the TLVs of each constituent is in mg/m3 and $f_s$ are the weight fraction of each chemicals, which is calculated as Y1 above.

Figure 8A:
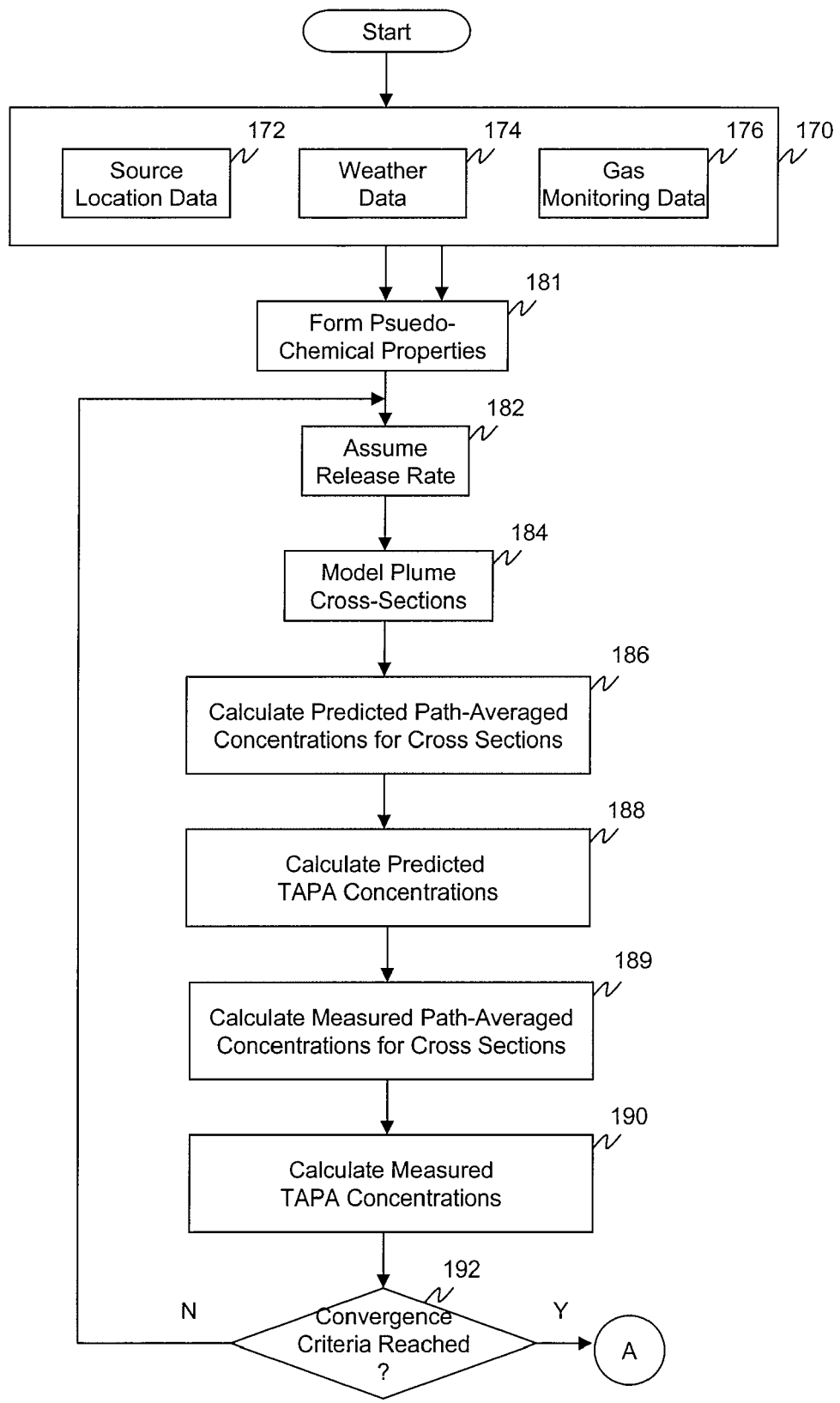
FIGS. 8A-8B are process flow diagrams of an open path release rate estimation algorithm for a multi-gas mixture according to one embodiment of the invention.
Figure 8B:
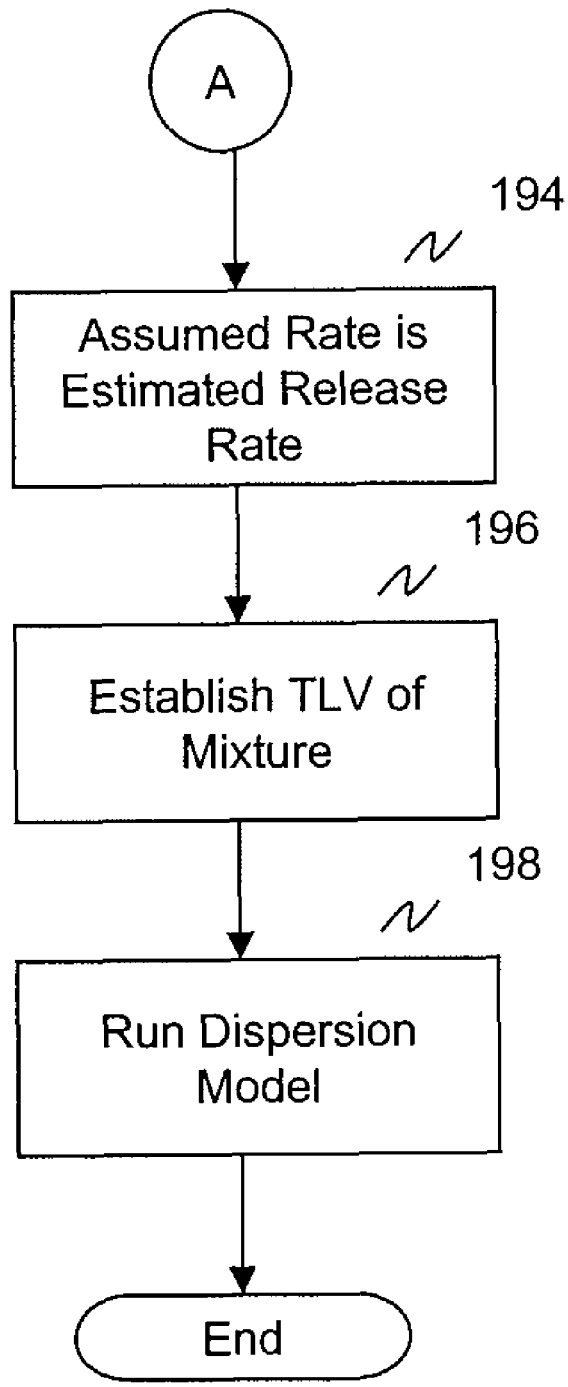

FIGS. 8A-8B are process flow diagrams of an open path release rate estimation algorithm for a multi-gas mixture according to one embodiment of the invention. The steps of the process may be implemented in the order indicated, or in any other order recognized by a person of skill in the art.

In step 170, various types of input data are gathered by the computer, including, for example, source location data 172, weather data 174, and gas monitoring data 176. The source location data and weather data are similar to the source location data 72 and weather data 74 described with reference to FIG. 6. The gas monitoring data 176 is also similar to the gas monitoring data 76 described with reference to FIG. 6, except that the data that is provided by each open-path sensing system include concentrations $C_1$(ppm-m), $C_2$(Ppm-m), $C_3$(Ppm-m), . . . , $C_n$(ppm-m) for N chemical components making up a chemical composition.

In step 181, based on the measured concentration values received from the open-path sensing systems, the computer 16 dynamically forms pseudo-chemical properties of gas mixture, for example, molecular weight, heat of vaporization, etc. based on the mixing rule.

Processing then proceeds to the back calculation process in steps 182-194 for each of the open-path sensing systems for the chemical mixture, which is similar to the back calculation process of steps 82-94 in FIG. 6.

Once the estimated release rate is obtained for the chemical composition, a toxic level value (TLV) is established for the mixture in step 196, based on the obtained pseudo-chemical properties. In step 198, the estimated release rate is provided to the dispersion model for overall plume effect.

Although this invention has been described in certain specific embodiments, those skilled in the art will have no difficulty devising variations to the described embodiment which in no way depart from the scope and spirit of the present invention. For example, while the system described herein uses open-path sensing systems for obtaining concentration measurements, a person of skill in the art should recognize that such systems may be used in conjunction with other sensors, such as, for example, point, PID, electro-chemical, paper tape, and the like.

Furthermore, to those skilled in the various arts, the invention itself herein will suggest solutions to other tasks and adaptations for other applications. It is the Applicant's intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

What is claimed is:

1. A computer-implemented substance release estimation method for a substance released into a surrounding medium thereby creating a plume, the method comprising:
    calculating a plurality of path-averaged concentration measurements of the substance for a plurality of time instants of a specific time window;
    averaging the plurality of path-averaged concentration measurements over the plurality of time instants of the specific time window to obtain a time-averaged measurement of the plurality of path-averaged concentration measurements;
    generating by a computer device a release rate of the substance estimated for the specific time window as a function of the time-averaged measurement of the plurality of path-averaged concentration measurements;
    associating the estimated release rate with a time reflective of the specific time window for which the estimated release rate was generated; and
    generating by the computer device an output based on the estimated release rate.

2. The computer-implemented substance release estimation method of claim 1 further comprising:
    selecting, by the computer device, a release rate assumed for the substance;
    modeling the plume based on the assumed release rate; and
    predicting a width of the plume based on the modeling of the plume and the specific time window.

3. The computer-implemented substance release estimation method of claim 2, wherein the modeling adjusts to changes to atmospheric conditions including wind direction, wind speed and stability, over time.

4. The computer-implemented substance release estimation method of claim 1, wherein the calculating the plurality of path-averaged concentration measurements comprises:
    collecting a plurality of path-averaged concentrations of the substance measured at each of the plurality of time instants over the specific time window.

5. The computer-implemented substance release estimation method of claim 4, wherein the collecting the plurality of concentrations comprises:
    transmitting a beam of light; and
    determining an amount of the light absorbed by the substance along the path of the beam.

6. The computer-implemented substance release estimation method of claim 5, wherein the generating the estimated release rate further comprises:
    selecting, by the computer device, a release rate assumed for the substance;
    predicting one or more path-averaged concentrations of the substance over the specific time window and over a width of the plume based on the assumed release rate, wherein the width of the plume is determined based on an intersection of the plume with the beam of light;
    averaging the predicted path-averaged concentrations over the plurality of time instants to generate a time-averaged prediction of the predicted path-averaged concentrations;
    comparing the time-averaged prediction of the predicted path-averaged concentrations with the time-averaged measurement of the plurality of path-averaged concentration measurements; and
    selecting, by the computer device, the assumed release rate as the estimated release rate of the substance based on the comparing.

7. The computer-implemented substance release estimation method of claim 1, wherein the substance is a single gas.

8. The computer-implemented substance release estimation method of claim 1, wherein the substance is a chemical mixture including a plurality of gases.

9. The computer-implemented substance release estimation method of claim 8 further comprising:
    receiving concentration measurements of each of the plurality of gases from at least one open-path sensor; and
    dynamically identifying chemical properties of the chemical mixture based on the received concentration measurements, wherein the estimated release rate is for the chemical mixture.

10. The computer-implemented substance release estimation method of claim 1 further comprising:
- generating by the computer device a release rate estimated for each of a plurality of time windows;
- associating each of the estimated release rates with a time reflective of the particular time window for which the estimated release rate was generated; and
- providing each of the plurality of estimated release rates and the time associated with each estimated release rate to a dispersion model for estimation of plume impact of the substance.

11. The computer-implemented substance release estimation method of claim 1, wherein the generating the release rate estimated for the specific time window includes:
- selecting, by the computer device, a release rate assumed for the substance;
- generating time-averaged predicted concentration measurements over the specific time window based on the assumed release rate;
- determining, by the computer device, whether there is a match, within a set tolerance level, of the time-averaged measurement of the plurality of path-averaged concentration measurements with the time-averaged predicted concentration measurement, for the specific time window; and
- outputting, by the computer device, the assumed release rate as the estimated release rate.

12. The computer-implemented substance release estimation method of claim 1, wherein the output is a display of plume impact of the substance.

13. A substance release estimation system for a substance released into a surrounding medium thereby creating a plume, the system comprising:
- at least one sensing system configured to collect a plurality of concentrations of the substance measured at each of a plurality of time instants of a specific time window; and
- a computer operably coupled to the at least one sensing system, the computer configured to execute computer program instructions stored in memory, the program instructions including:
  - calculating a plurality of path-averaged concentration measurements based on the collected plurality of concentrations over the specific time window;
  - averaging the plurality of path-averaged concentration measurements over the plurality of time instants of the specific time window to obtain a time-averaged measurement of the plurality of path-averaged concentration measurements;
  - generating a release rate of the substance estimated for the specific time window as a function of the time-averaged measurement of the plurality of path-averaged concentration measurements;
  - associating the estimated release rate with a time reflective of the specific time window for which the estimated release rate was generated; and
  - generating an output based on the estimated release rate.

14. The substance release estimation system of claim 13, wherein the computer program instructions further include:
- selecting a release rate assumed for the substance;
- modeling the plume based on the assumed release rate; and
- predicting a width of the plume based on the modeling of the plume and the specific time window.

15. The substance release estimation system of claim 14, wherein the modeling adjusts to changes to atmospheric conditions including wind direction, wind speed, and stability, over time.

16. The substance release estimation system of claim 13, wherein the computer program instructions for calculating the plurality of path-averaged concentration measurements comprise:
- collecting a plurality of path-averaged concentrations of the substance measured at each of the plurality of time instants over the specific time window.

17. The substance release estimation system of claim 16, wherein the program instructions for collecting the plurality of concentrations comprise:
- transmitting a beam of light; and
- determining an amount of the light absorbed by the substance along the path of the beam.

18. The substance release estimation system of claim 17, wherein the program instructions for estimating the release rate further comprises:
- selecting a release rate value assumed for the substance;
- predicting one or more path-averaged concentrations of the substance over the specific time window and over a width of the plume based on the assumed release rate, wherein the width of the plume is determined based on an intersection of the plume with the beam of light;
- comparing the time-averaged prediction of the predicted path-averaged concentrations with the time-averaged measurement of the plurality of path-averaged concentration measurements; and
- selecting the assumed release rate as the estimated release rate of the substance based on the comparing.

19. The substance release estimation system of claim 13, wherein the substance is a single gas.

20. The substance release estimation system of claim 13, wherein the substance is a chemical mixture including a plurality of gases.

21. The substance release estimation system of claim 20, wherein the program instructions further comprise:
- receiving concentration measurements of each of the plurality of gases from the at least one sensing system; and
- dynamically identifying chemical properties of the chemical mixture based on the received concentration measurements, wherein the estimated release rate is for the chemical mixture.

22. The substance release estimation system of claim 13, wherein the sensing system includes an open-path sensor.

23. The substance release estimation system of claim 13, wherein the sensing system includes both fixed point and open-path sensors.

24. A non-transitory computer readable media embodying program instructions for execution by a processing device, the program instructions adapting the processing device for substance release estimation for a substance released into a surrounding medium thereby creating a plume, the program instructions comprising:
- calculating a plurality of path-averaged concentration measurements of the substance for a plurality of time instants of a specific time window;
- averaging the plurality of path-averaged concentration measurements over the plurality of time instants of the specific time window to obtain a time-averaged measurement of the plurality of path-averaged concentration measurements;
- predicting one or more path-averaged concentrations of the substance over the specific time window and over a width of the plume based on an assumed release rate, wherein the width of the plume is determined based on an intersection of the plume with a beam of light;

comparing a time-averaged prediction of the predicted path-averaged concentrations with a time-averaged measurement of the plurality of path-averaged concentration measurements; and selecting the assumed release rate as the estimated release rate of the substance based on the comparing.

* * * * *